United States Patent [19]

Galpin et al.

[11] Patent Number: 5,739,109
[45] Date of Patent: Apr. 14, 1998

[54] METHOD OF TREATING NEUROINFLAMMATORY DEGENERATIVE DISEASES

[75] Inventors: Jeffrey E. Galpin; Dennis A. Casciato, both of Hidden Hills, Calif.; Michael A. Davis, Westwood, Mass.; Saul M. Levin, Washington, D.C.; MerriBeth Adams, St. James, N.Y.; Candace B. Pert; Michael R. Ruff, both of Potomac, Md.; Gary Globe, Stevenson Ranch, Calif.

[73] Assignee: Advanced Immunit Inc., Stony Brook, N.Y.

[21] Appl. No.: 608,434

[22] Filed: Feb. 28, 1996

Related U.S. Application Data

[63] Continuation-in-part of Ser. No. 346,334, Nov. 29, 1994, Pat. No. 5,567,682, which is a continuation of Ser. No. 44,903, Apr. 6, 1993, abandoned, which is a continuation of Ser. No. 831,088, Feb. 7, 1992, abandoned, which is a continuation of Ser. No. 551,048, Jul. 11, 1990, abandoned, which is a continuation of Ser. No. 285,074, Dec. 16, 1988, abandoned.

[51] Int. Cl.$^6$ ............................ A61K 38/07; A61K 38/08
[52] U.S. Cl. .............................. 514/15; 514/16; 514/17; 514/18
[58] Field of Search ............................ 514/15, 16, 17, 514/18; 530/328, 329, 330

[56] References Cited

U.S. PATENT DOCUMENTS

| | | | |
|---|---|---|---|
| 5,063,206 | 11/1991 | Bridge et al. | 514/16 |
| 5,189,022 | 2/1993 | Bridge et al. | 514/16 |
| 5,192,753 | 3/1993 | McGeer et al. | 514/569 |
| 5,194,448 | 3/1993 | Coupland et al. | 514/558 |
| 5,248,667 | 9/1993 | Bridge et al. | 514/15 |
| 5,276,016 | 1/1994 | Pert et al. | 514/15 |
| 5,434,170 | 7/1995 | Andrulis, Jr. | 514/264 |
| 5,446,026 | 8/1995 | Ruff et al. | 514/15 |
| 5,534,495 | 7/1996 | Pert et al. | 514/16 |
| 5,545,656 | 8/1996 | Loose et al. | 514/418 |
| 5,550,132 | 8/1996 | Benson et al. | 514/269 |
| 5,567,682 | 10/1996 | Pert | 514/15 |
| 5,593,991 | 1/1997 | Adams et al. | 514/235.2 |
| 5,686,417 | 11/1997 | MacFadden et al. | 514/16 |

FOREIGN PATENT DOCUMENTS

| | | |
|---|---|---|
| 0 249 390 A2 | 12/1987 | European Pat. Off. |
| 0 249 394 A2 | 12/1987 | European Pat. Off. |
| 0 579 363 A1 | 1/1994 | European Pat. Off. |
| WO 87/07614 | 12/1987 | WIPO |
| WO92/14751 | 9/1992 | WIPO |
| 9320102 | 10/1993 | WIPO |

OTHER PUBLICATIONS

Pert, et al. AIDS and Its Dementia as a Neuropeptide Disorder: Role of VIP Receptor Blockade by Human Immunodificiency Virus Envelope, Annals of Neurology Suppl. to vol. 23, 1988, pp. 571–573.

Bridge, et al. PHASE I of Peptide T in Aids Patients and Controls, International Conference on Aids, Jun. 12–16, 1988 Stockholm, Sweden.

Heseltine, et al. Phase I of Peptide T in Aids: Pharmacology and Immune Response, INt'l Conference on Aids, Jun. 12–16, 1988, Stockholm, Sweden.

Jaffe, et al., Isolation and Identification of a Peptide form Rat Brain Which INhibits [3H]TCP Binding, Int. J. Biochem. vol. 22, No. 3, pp. 239–245, 1990.

Michael R. Ruff, et al., Pharmacokinetics of Peptide T in Patients with Acquired Immunodeficiency Syndrome (Aids), Prog. Neuro-Psychopharmacol & Biol. Psychiat. 1991, vol. 15, pp. 791–801.

Ruff, et al. Cytokine Changes in Adult HIV Patients Receiving Peptide T, Portland, 1994.

D.J. Socci, et al., Chronic Peptide T Administration Prevents Neocortical Atrophy Resulting from Nucleus Basalis Lesions in Aged Rats, Society for Neurocience Abstracts, vol. 18, 1992.

J.A. Marcusson, et al., Peptide–T in the Treatment of Psoriasis and Psoriatic Arthritis, A case report, Acta Derm Venereol (Stockh) 69, 1989, pp. 86–88.

Rodgers–Johnson, et al., Tropical Spastic Paraparesis and HTLV–I–Associated Myelopathy–Clinical and Laboratory Diagnosis, Human Retrovirology: HTLV edited by W.A. Blattner, Raven Press, Ltd., NY 1990, pp. 205–211.

Marcusson, et al., Peptide T and Psoriasis, Acta Derm Venereol (Stockh) 1989; Suppl. 146: 117–121.

Ruff, et al., CD4 receptor binding peptides that block HIV infectivity cause human monocyte chemotaxis, FEB 04365, vol. 211, No. 1, 17–22, Jan. 1987.

Raj, et al., Identification and Characterization of a Novel GGA/C–Binding Protein, GBP-i, That is Rapidly Inducible by Cytokines, Molecular and Cellular Biology, Dec. 1994, pp. 7770–7781.

Dalgleish, et al., The CD4 (T4) antigen is an essential component of the receptor for the AIDS retrovirus, Nature, vol. 312 20/27 Dec. 1994, pp. 763–7.

Brenneman, et al., Neuronal cell killing by the envelope protein of HIV and its prevention by vasoactive intestinal peptide, Nature, vol. 353, No. 6191, pp. 639–642, 13 Oct. 1988.

Pert, et al., Octapeptides deduced from the neuropeptide receptor–like pattern of antigen T4 in brain potently inhibit human immunodeficiency virus receptor binding and T–cell infectivity, Porc. Natl. Acad Sci. USA, vol. 83, pp. 9254–9258, Dec. 1986, Neurobiology.

Pert, et al., Neuropeptides and their Receptors: A Psychosomatic Network, The Journal of Immunology, vol. 135, No. 2, Aug. 1985, pp. 820s–826s.

Nagano et al. Expression of cytokines in brain lesions . . . Neurology, Apr. 1994, vol. 44, pp. 710–715.

*Primary Examiner*—Jeffrey E. Russel
*Attorney, Agent, or Firm*—McAulay Fisher Nissen Goldberg & Kiel, LLP

[57] ABSTRACT

The present invention relates to a method of treating neuroinflammatory degenerative diseases which are cytokine mediated. The method involves administration of an effective amount of Peptide T or a related Peptide to diminish, halt or reverse the patient's loss of function due to neuroinflammation.

7 Claims, No Drawings

5,739,109

METHOD OF TREATING NEUROINFLAMMATORY DEGENERATIVE DISEASES

CROSS REFERENCE TO RELATED APPLICATIONS

This application is a continuation in part of application Ser. No. 08/346,334 filed Nov. 29, 1994, now U.S. Pat. No. 5,567,682, which was a continuation of application Ser. No. 08/044,903 filed Apr. 6, 1993, now abandoned, which was a continuation of application Ser. No. 07/831,088 filed Feb. 7, 1992, now abandoned, which was a continuation of application Ser. No. 07/551,048 filed Jul. 11, 1990, now abandoned, which was a continuation of application Ser. No. 07/285,074 filed Dec. 16, 1988, now abandoned.

TECHNICAL FIELD

This invention relates to the treatment of neuroinflammatory degenerative diseases and more particularly to neuroinflammatory degenerative diseases which are cytokine mediated.

BACKGROUND OF THE INVENTION

Progressive multifocal leukoencephalopathy (PML) is a rare afebrile demyelinating disease of cerebral white matter characterized by multiple, discrete foci of disease. A papovavirus, JC virus, is consistently identified in oligodendrocytes in affected areas, and is believed to be one cause of PML. The symptoms of PML include headache, ataxia, hemiparesis, confusion, and other mental status changes. Computed tomography scans most often reveal nonenhancing, low-density lesions of the periventricular white matter. Magnetic resonance imaging scans show high-signal intensity lesions without enhancement. Cerebrospinal fluid studies are usually unrevealing; the diagnosis is established by brain biopsy. JC virus can be identified by typical electron microscopy morphology, by immunofluorescence staining, or by gene amplification techniques. Clinically, patients deteriorate progressively. Death occurs on average in less than 3 months, although spontaneous remission has been reported.

JC and BK viruses (JCV and BKV) are human polyomaviruses. Infections with these viruses appear to be widespread, but asymptomatic in the majority of patients. JCV or BKV infection apparently is acquired during childhood and persists in the kidney. Approximately 60–80 percent of adults in the United States and Europe have antibodies to JCV and/or BKV. However, the incidence of HIV infection has significantly altered the epidemiology of PML.

In the pre-HIV era, PML was seen primarily in older patients with underlying hematologic malignancies. PML was also sometimes seen in patients with other causes for depression of cell-mediated immunity, such as steroid use. Rarely, patients have been described who developed PML in the absence of any identifiable immunodeficiency.

Reported deaths due to PML have significantly increased with the rise in AIDS cases, from 1.5/10,000,000 persons in 1974 to 6.1/10,000,000 persons in 1987. It is estimated that over half of the deaths due to PML are associated with HIV infection and that approximately 1–4 percent of patients with HIV infection will develop PML.

The neuropathologic findings of PML are most likely a result of direct infection of the oligodendrocytes with JCV, leading to decreased myelin production and demyelination. Electron microscopy and in situ hybridization have been used to demonstrate the presence of polyomavirus in oligodendrocyte nuclei. BK and JC viruria can be seen in patients with a variety of immunodeficiencies, but appears to be most frequent among renal and bone marrow transplant recipients. In addition, pregnant women may excrete JCV or BKV in third trimester, perhaps related to defects in cell-mediated immunity observed during pregnancy.

Newer research strongly suggests that PML is in large part an inflammatory disorder. Accumulating evidence shows that adhesion molecules are critically involved in inflammatory demyelination in the focusing of systemic immune responses into the target issue, the nervous system. Adhesion molecules are unregulated through the action of cytokines, a heterogeneous group of human proteins that are active at low concentrations to regulate cell growth, differentiation and function. Tumor necrosis factor alpha appears to be of prime importance.

Circulating adhesion molecules probably reflect acute inflammatory episodes in the central and peripheral nervous system, but may also function to modulate ongoing inflammatory responses. Cytokines released by THI cells render resident and immigrant macrophages, as well as microglia, activated to synthesize and release increased amounts of inflammatory mediators, such as oxygen radicals, nitric oxide metabolites, and components of the complement system. A more detailed understanding of the sequence of immunopathologic events that culminate in myelin damage in the central and peripheral nervous systems has revealed several sites to which more specific and effective immunointervention can be targeted.

Cytokines participate in normal physiologic events within the central nervous system. At time of infection and inflammation, their role is emphasized by the unregulation of cytokines and their receptors within the central nervous system, with concomitant effects on brain function.

Cytokines produced by glial cells, T cells, and macrophages interact within the central nervous system to determine the outcome of the inflammatory reaction. Cytokines have been implicated in the pathogenesis of many neuroinflammatory degenerative diseases, including multiple sclerosis (MS), and amyotrophic lateral sclerosis (ALS), as well as PML. Though no link has been made, their role continues to be intensely investigated.

The microglial cell is the central nervous system representative of the peripheral macrophage. The central nervous system is far more sensitive to immune inflammtory modulators which probably are practical responses to toxins, tumors and infections. It is when these inflammatory modulators are dysregulated in these diseases that true damage through demyelination and neuronal growth toxicity may occur.

Treatment of cultures of myelinated cells with inflammatory cytokines results in a marked reduction in myelin based protein. Microglial reactive damaged nodules are clearly evident and a characteristic of PML. Normal brain sections show no reactivity for any of the cytokines while PML tissue demonstrates the clear presence of at least IL-6, TNF, and interferon-gamma. Inhibiting specific cytokines and forms of mitogenesis may also act to stabilize activation of virus and protect the host from immune mediated damage induced by the virus or its products and/or effects.

Peptide T is a short peptide fragment capable of blocking the binding of gp120 to neurons or lymphocytes. This blocks entry of virus into a cell through CD4 receptors and blocks the toxic effects of gp120 on specific types of cells and tissues.

DESCRIPTION OF THE INVENTION

Described is a method of treating neuroinflammatory diseases which are cytokine mediated in which a person suffering from such a disease, for example, PML, is administered a therapeutically effective amount of a peptide of the formula:

R$^a$-Ser-Thr-Thr-Thr-Asn-Tyr-R$^b$  (I)

where R$^a$ represents an amino terminal residue Ala- or D-Ala- and R$^b$ represents a carboxyl terminal residue -Thr or Thr amide, and/or an additional Cys-residue at one or both of the amino and carboxyl terminals, or a peptide of the formula:

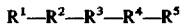
R$^1$—R$^2$—R$^3$—R$^4$—R$^5$  (II)

where R$^1$ is an amino terminal residue Thr-, Ser-, Asn-, Leu-, Ile-, Arg- or Glu-; R$^2$ is Thr, Ser or Asp; R$^3$ is Thr, Ser, Asn, Arg, Gln, Lys or Trp; R$^4$ is Tyr; and R$^5$ is a carboxyl terminal amino group, a corresponding D-amino acid as the amino terminal residue, and/or a corresponding amide derivative at the carboxyl terminal residue and/or additionally a Cys-residue at one or both of the amino and carboxyl terminals, or a physiologically acceptable salt thereof. Also the peptide may have the formula X-R$^1$—R$^2$—R$^3$—R$^4$—R$^5$-X, where R$^1$-R$^5$ are as defined above and X is cysteine.

Preferred peptides are

- ala-ser-thr-thr-thr-asn-tyr-thr, thr-thr-asn-tyr-thr,
- ser-ser-thr-tyr-arg, asn-thr-ser-tyr-thr,
- thr-thr-ser-tyr-thr, ser-ser-thr-tyr-arg,
- asn-thr-ser-tyr-gly, ser-thr-asn-tyr-arg,
- ser-ser-thr-tyr-arg, ser-ser-arg-tyr-arg,
- ser-ser-thr-tyr-arg, thr-thr-ser-tyr-ser, and
- cys-thr-thr-asn-tyr-thr-cys.

The peptide is preferably conjugated to a protein, such as human serum albumin. Preferably, the peptide is ASTTTNYT, also known as Peptide T.

The selected peptide is administered in a therapeutically effective amounts that is an amount sufficient to diminish, halt or to reverse the patient's loss of function due to neuro-inflammation. Usually, the amount administered is an amount of from 0.2 to 50 mg, preferably 0.2 to 30 mg per day for a 70 kg adult human. The peptide may be formulated for oral, buccal, parenteral, topical, intranasal or rectal administration.

Also disclosed is a method of arresting the degeneration and loss of cerebral function in a person having a neuroinflammatory disease which is cytokine mediated comprising administering to that person a therapeutically effective amount of a peptide of the formula:

R$^a$-Ser-Thr-Thr-Thr-Asn-Tyr-R$^b$  (I)

where R$^a$ represents an amino terminal residue Ala- or D-Ala- and R$^b$ represents a carboxyl terminal residue -Thr or Thr amide, and/or an additional Cys-residue at one or both of the amino and carboxyl terminals, or a peptide of the formula:

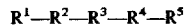
R$^1$—R$^2$—R$^3$—R$^4$—R$^5$  (II)

where R$^1$ is an amino terminal residue Thr-, Ser-, Asn-, Leu-, Ile-, Arg- or Glu-; R$^2$ is Thr, Ser or Asp; R$^3$ is Thr, Ser, Asn, Arg, Gln, Lys or Trp; R$^4$ is Tyr; and R$^5$ is a carboxyl terminal amino group, a corresponding D-amino acid as the amino terminal residue, and/or a corresponding amide derivative at the carboxyl terminal residue and/or additionally a Cys-residue at one or both of the amino and carboxyl terminals, or a physiologically acceptable salt thereof, and continuing the administration on a maintenance basis to prevent or diminish further degeneration of cerebral function.

Preferably, the peptide is administered in an amount such that demyelinating of the oligodendrocytes, macroplates and microglia, is at least reduced or stabilized, the peptide acting as an anticytokine modulator to stop the effects of the inflammation, even in the continued presence of the virus.

While not wishing to be bound to any particular theory or mode of operation, the short chain peptides described herein, notably Peptide T, are believed to inhibit cytokines to stabilize activation of the virus and protect the host from damage.

Peptide T may be potentially of significant benefit to the host in preventing disease progression through mediation of viral and dysfunctional immune activation. It is theoretically possible that an uneasy truce may be maintained with viral presence without further damaging the host.

Peptide T may regulate a turned on immune system which is damaging itself through its friendly fire inflammatory response. Peptide T may also stimulate IL-2 and IL-10 production which would reregulate or down regulate the inflammation and perhaps act protectively in PML, or other neuroinflammatory degenerative diseases.

Peptide T also is believed to have an effect on reducing neuronal cell death or injury mediated by certain cytokines. By both binding CD4 receptor and mediating or down regulating certain cytokines. Peptide T may offer therapy to autoimmune disease where thermostat activation—inactivation balance is distorted and over activation takes precedence.

Treating PML with a drug such as Peptide T offers an innovative approach to an illness with no effective treatment. Even a modest clinical effect would be considered a major milestone.

The use of peptides as herein described are believed to be of most therapeutic benefit as a prophylactic when given early in the degenerative course of the disease to prevent further deterioration.

The peptides used in the therapeutic procedures of this invention are known materials and are described as relatively small or short peptides of up to 30 amino acids having the general formula:

R$^a$-Ser-Thr-Thr-Thr-Asn-Tyr-R$^b$  (I)

where R$^a$ represents an amino terminal residue Ala- or D-Ala- and R$^b$ represents a carboxyl terminal residue -Thr or -Thr amide or a derivative thereof, with an additional Cys-residue at one or both of the amino and carboxyl terminals, or a peptide of the formula:

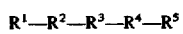
R$^1$—R$^2$—R$^3$—R$^4$—R$^5$  (II)

where R$^1$ is an amino terminal residue Thr-, Ser-, Asn-, Leu-, Ile-, Arg- or Glu-; R$^2$ is Thr, Ser or Asp; R$^3$ is Thr, Ser, Asn, Arg, Gln, Lys or Trp; R$^4$ is Tyr; and R$^5$ is a carboxyl terminal amino group or a derivative thereof with a corresponding D-amino acid as the amino terminal residue, and/or a corresponding amide derivative at the carboxyl terminal residue and/or additionally a Cys-residue at one or both of the amino and carboxyl terminals.

Physiologically acceptable salts of these peptides are also included. Also the peptide may have the formula $X-R^1-R^2-R^3R^4-R^5-X$ where $R^1-R^5$ are as defined above and X is cysteine.

Preferred peptide are ala-ser-thr-thr-thr-asn-tyr-thr, thr-thr-asn-tyr-thr, ser-ser-thy-tyr-arg, asn-thr-ser-tyr-thr, thr-thr-ser-tyr-thr, ser-ser-thr-tyr-arg, asn-thr-ser-tyr-gly, ser-thr-asn-tyr-arg, ser-ser-thr-tyr-arg, ser-ser-arg-tyr-arg, ser-ser-thr-tyr-arg, thr-thr-ser-tyr-ser, and cys-thr-thr-asn-tyr-thr-cys.

The peptide is preferably conjugated to a protein, such as human serum albumin.

The pre